United States Patent [19]

Seberg

[11] 4,192,305

[45] Mar. 11, 1980

[54] CATHETER PLACEMENT ASSEMBLY HAVING AXIAL AND ROTATIONAL ALIGNMENT MEANS

[75] Inventor: Charles H. Seberg, Libertyville, Ill.

[73] Assignee: Abbott Laboratories, North Chicago, Ill.

[21] Appl. No.: 935,441

[22] Filed: Aug. 21, 1978

[51] Int. Cl.² .............................................. A61M 5/00
[52] U.S. Cl. .............................. 128/214.4; 128/214.2; 128/348; 128/349 R; 128/DIG. 16
[58] Field of Search ............... 128/214.4, 214 R, 348, 128/349, 221, 214.2, DIG. 16

[56] References Cited

U.S. PATENT DOCUMENTS

| Re. 27,797 | 10/1973 | Sorenson et al. | 128/214.4 |
|---|---|---|---|
| 3,589,361 | 6/1971 | Loper | 128/214.4 |
| 3,720,210 | 3/1973 | Diettrich | 128/214.4 |
| 3,769,975 | 11/1973 | Nimoy et al. | 128/214.4 |
| 3,782,383 | 1/1974 | Thompson | 128/214 R |
| 3,809,081 | 5/1974 | Loveless | 128/214.4 |
| 3,867,937 | 2/1975 | Schwartz | 128/214.4 |
| 3,906,946 | 9/1975 | Nordstrom | 128/214.4 |
| 4,068,659 | 1/1978 | Moorehead | 128/214 |
| 4,106,506 | 8/1978 | Koehn et al. | 128/214.4 |
| 4,129,128 | 12/1978 | McFarlane | 128/214 R X |

Primary Examiner—Henry K. Artis
Attorney, Agent, or Firm—Robert L. Niblack; Aaron L. Hardt; Robert S. Beiser

[57] ABSTRACT

A needle-inside, catheter placement assembly including a needle and a catheter unit comprising a catheter, winged catheter insertion means, flexible tubing and tube hub, wherein axial and rotational alignment of the needle and catheter unit are maintained by mechanically interlocked complementary means associated with the needle and lumen of the winged catheter insertion means. Means for removably connecting the proximal ends of the catheter unit and needle to stretch the flexible tubing tautly are also provided.

14 Claims, 19 Drawing Figures

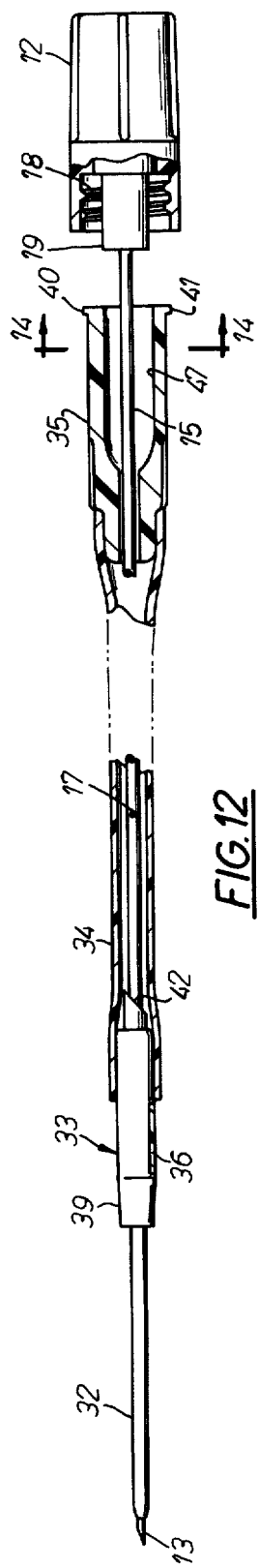
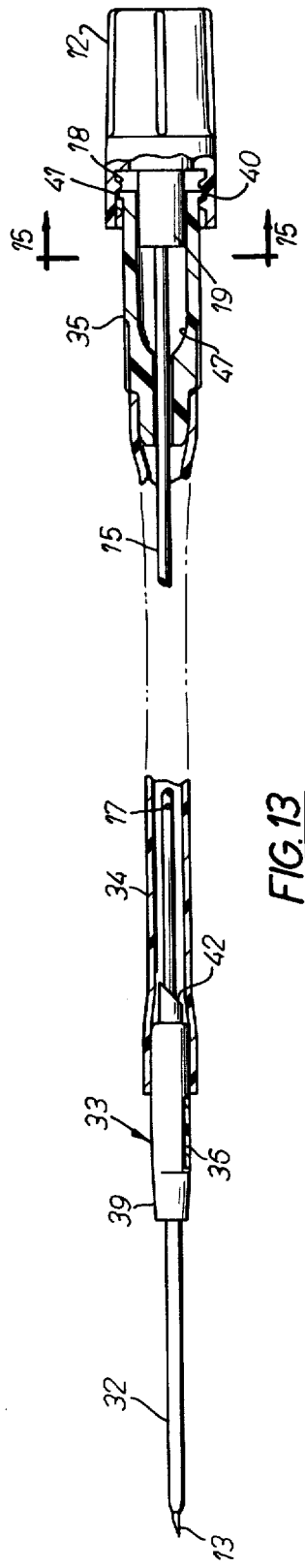
FIG. 12
FIG. 14
FIG. 15
FIG. 13

CATHETER PLACEMENT ASSEMBLY HAVING AXIAL AND ROTATIONAL ALIGNMENT MEANS

BACKGROUND OF THE INVENTION

The present invention relates to intravenous catheter placement assemblies and, more particularly, to needle-inside, catheter placement assemblies having axial and rotational alignment means.

Catheter placement assemblies of the needle-inside type are well known in the prior art. U.S. Pat. No. 3,312,200 granted to M. Eisenberg on Apr. 4, 1967 discloses such a catheter placement assembly. U.S. Pat. No. 3,809,081 granted to J. Loveless on May 7, 1974 discloses such a catheter placement assembly having an obturator threadably connected to the catheter hub. U.S. Pat. No. 3,589,361 granted to D. Loper on June 10, 1968 discloses such a catheter placement assembly having axially movable winged insertion means disposed on the catheter. U.S. Pat. No. 3,769,975 granted to M. Nimoy, et al. on Nov. 6, 1973 discloses such a catheter placement assembly having a catheter unit comprising a catheter, winged catheter insertion means, flexible tubing and a tube tub.

An advantage of the Nimoy catheter placement assembly is that its tube hub is substantially spaced from the venipuncture site, thereby allowing the catheter to be securely attached to the patient at that site and allowing possible infection causing connections to an intravenous solution set to be made remote from the wound.

A major disadvantage of the Nimoy assembly is that axial and rotational alignment of the needle and catheter unit is difficult to maintain both prior to and during placement of the catheter into a patient. Nimoy attempts to solve this problem by the use of a removable plastic sleeve removably mounted on the flexible tubing. Loper discloses that flexing of his winged insertion means grasps both the catheter and needle during venipuncture. U.S. Pat. No. 3,537,451 granted to D. Beck, et al. on Nov. 3, 1970 discloses still another winged catheter insertion means which grasps both the catheter and their two-diametered needle during venipuncture.

Unfortunately, these prior art assemblies do not maintain axial or rotational alignment of the needle and catheter unit prior to placement of the catheter into the patient. Thus, proper axial or rotational alignment of the needle and catheter must be made by the user of the assembly just prior to venipuncture. Accordingly, it will be apparent that such a catheter placement assembly providing axial and rotational alignment of the needle and catheter unit thereof at all times would be advantageous and desirable.

SUMMARY OF THE INVENTION

Therefore, it is the primary object of this invention to provide a needle-inside, catheter placement assembly wherein the needle and catheter unit thereof are maintained in axial and rotational alignment at all times during their assemblage. Another object is to provide such an assembly wherein the flexible portion of the catheter unit is stretched taut until venipuncture is completed.

In accordance with these and other objects, there is provided by the present invention a needle-in-side, catheter placement assembly wherein the needle and catheter unit thereof are maintained in axial and rotational alignment at all times during their assemblage by mechanically interlocked complementary means associated with the needle and lumen of the winged catheter insertion means. Means for removably connecting the proximal ends of the catheter unit to stretch the flexible tubing tautly are also provided.

BRIEF DESCRIPTION OF THE DRAWING

Other objects and attendant advantages will be obvious to those skilled in the art by reading the following detailed description in connection with the accompanying drawing wherein like reference characters designate like or corresponding parts throughout the several figures thereof and wherein:

FIG. 12 is a broken, front elevational view, partially in cross-section of the assembly of FIG. 1 before the tube hub is threadably connected to the needle hub, FIG. 13 is a broken, front elevational view, partially in cross-section, of the assembly of FIG. 1 after the tube hub has been threadably connected to the needle hub, FIG. 14 is a cross-sectional view along the line 14—14 in FIG. 12 of the tube and needle hubs thereof, FIG. 15 is a cross-sectional view along the line 15—15 in FIG. 13 of the tube and needle hubs thereof.

DETAILED DESCRIPTION OF THE INVENTION

Figure 1:
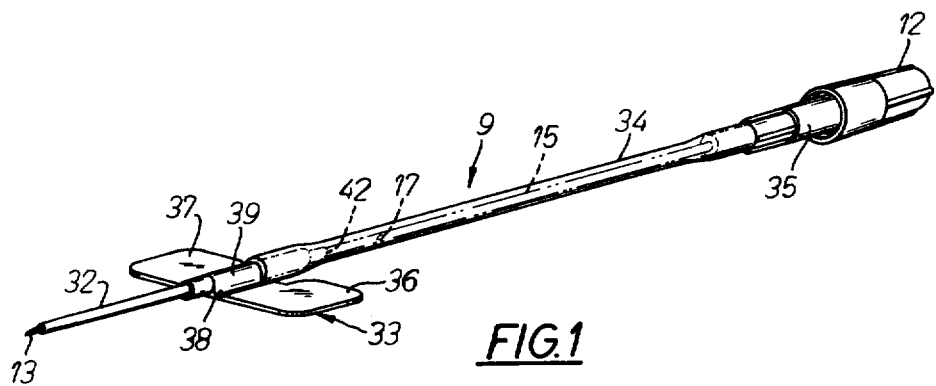
FIG. 1 is a perspective view of a preferred embodiment of the needle-inside, catheter placement assembly of the present invention.

Referring to the drawing, there is shown in FIG. 1 a preferred embodiment of the needle-inside, catheter placement assembly 9 of this invention. Catheter placement assembly 9 comprises a needle 11 having its proximal end attached to a needle hub 12 and a beveled, sharpened distal end 13.

Figure 2:
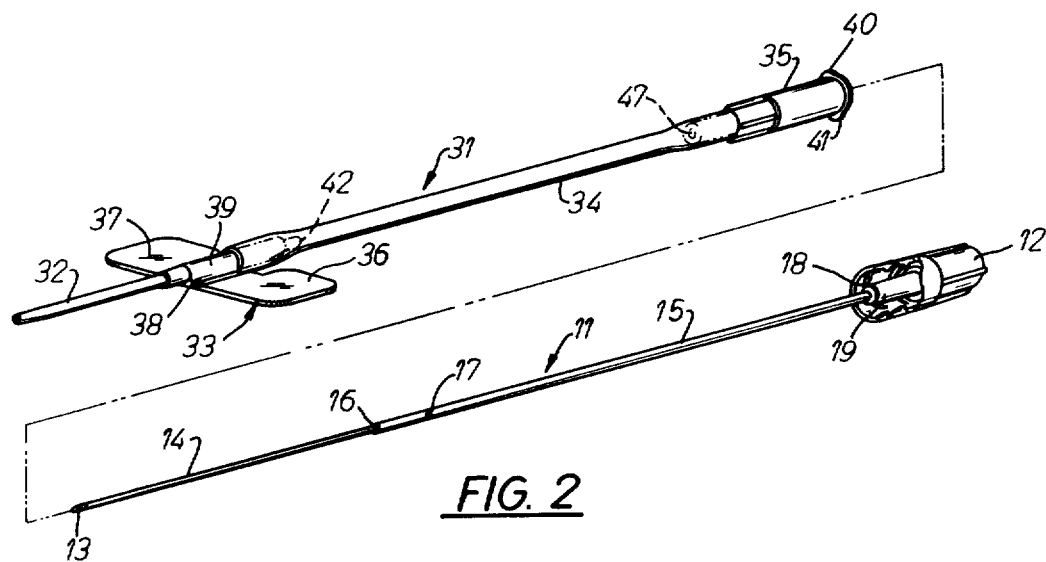
FIG. 2 is an exploded view of the assembly of FIG. 1 showing the catheter unit thereof and the needle with its hub partially in cross-section.
Figure 3:
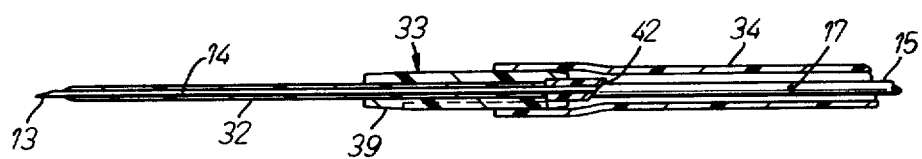
FIG. 3 is a cross-sectional view of a portion of the assembly of FIG. 1.

As shown in FIG. 2, needle 11 has a first portion 14 extending a predetermined distance from distal end 13 and coaxially joined to a second portion 15 which extends to the proximal end of needle 11. Second portion 15 has an outer diameter greater than the outer diameter of first portion 14 so that the distal endwall of second portion 15 forms a radial enlargement of needle 11 at the shoulder 16 between first portion 14 and second portion 15. Shoulder 16 is canted or oblique to the axis of needle 11.

Figure 4:
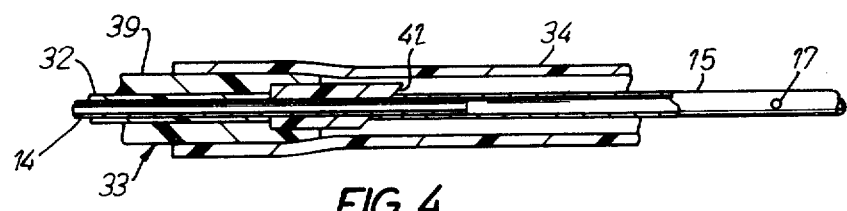
FIG. 4 is an enlargement of a portion of FIG. 3.

Preferably, needle 11 can be assembled from hollow stainless steel tubing, as best seen in FIG. 4. Second portion 15 consists of a hollow tube having an inner diameter substantially equal to the outer diameter of first portion 14 which is inserted into second portion 15 and swaged, or otherwise suitably attached, thereto. The distal end of second portion 15 is canted or oblique to the axis thereof.

Where needle 11 is hollow, second portion 15 will have an aperture 17 in its sidewall affording fluid communication from distal end 13 through first portion 14 and second portion 15 to aperture 17.

As shown in FIG. 2, needle hub 12 has an internal projection 19 to which the proximal end of needle 11 is attached. Needle hub 12 also has an internal thread 18 having a function that will be explained in greater detail in a following paragraph. Alternatively, needle hub 12 can be provided with a pair of L-shaped channels, see FIG. 17, or a pawl or lever, see FIG. 16, instead of thread 18.

Catheter placement assembly 9 further comprises a catheter unit 31 having a flexible plastic catheter 32, winged catheter insertion means 33, flexible tubing 34 and tube hub 35. Catheter 32 is distally tapered at its distal end and can be made of any biocompatible flexible plastic material such as polyethylene, polypropylene, polytetrafluoroethylene or polyvinylchloride. The inner diameter of catheter 32 is substantially identical to the outer diameter of first portion 14 of needle 11.

Winged catheter insertion means 33 has a pair of flexible wings 36, 37 which, preferably, have a weakened portion or groove 38 adjacent a tubular portion 39 which has a lumen therethrough. Preferably, winged catheter insertion means 33 can be made of polyvinylchloride, but any other material that will enable wings 36, 37 to be flexed upwardly for aiding in the insertion of catheter 32 into the patient and subsequently downwardly, if necessary, for taping to the patient's body can be used.

The proximal end of catheter 32 is in fluid communication with the distal end of the lumen of tubular portion 39. As shown in FIG. 1, catheter 32 has an outer diameter substantially equal to the inner diameter of the lumen of tubular portion 39 and is inserted therein. However, it will be readily apparent that tubular portion 39 can be designed to receive catheter 32 on its outer diameter, if it is so desired.

The distal end of flexible tubing 34 is in fluid communication with the lumen of tubular portion 39 at its proximal end. As shown in FIG. 1, tubular portion 39 is inserted into flexible tubing 34, but it will be readily apparent that flexible tubing 34 can be inserted into tubular portion 39, if so desired. Preferably, flexible tubing 34 can be made of clear polyvinylchloride or polyurethane and has an inner diameter greater than the inner diameter of catheter 32.

The proximal end of flexible tubing 34 is connected in fluid communication to tube hub 35 which has a lumen 47 therethrough. Tube hub 35 is, preferably, made of polyvinylchloride and, preferably, has a recess or female luer adapter at its proximal end. A collar having ears 40, 41 extends outwardly from the proximal endwall of tube hub 35.

As best seen in FIG. 4, the tubular portion 39 of winged catheter insertion means 33 has an external surface on its proximal end 42 that is complementary to shoulder 16 of needle 11. Proximal end 42 and shoulder 16 of needle 11 provide complementary means which mechanically interlock to provide axial and rotational alignment of needle 11 and catheter unit 31. As shown, proximal end 42 is preferably formed of a plastic insert molded into a recess from the lumen of tubular portion 39, which allows proximal end 42 to be made of a more rigid material than the remainder of insertion means 33, if so desired. Alternatively, tubular portion 39 can be molded as a single piece, without need of an insert, if the material used for all of insertion means 33 will provide sufficient rigidity for proximal end 42.

Figure 5:
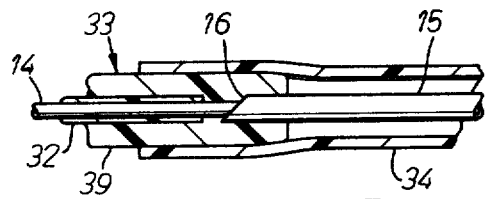
FIG. 5 is another embodiment of the needle-inside, catheter placement assembly of the present invention when viewed as in FIG. 4.

FIG. 5 depicts an alternative embodiment of the complementary means associated with the lumen of tubular portion 39 and needle 11 to mechanically interlock catheter unit 31 and needle 11 in axial and rotational alignment while assembled. In this embodiment, the proximal end of the lumen of tubular portion 39 is enlarged to form a recess complementary to shoulder 16 of needle 11.

Figure 6:
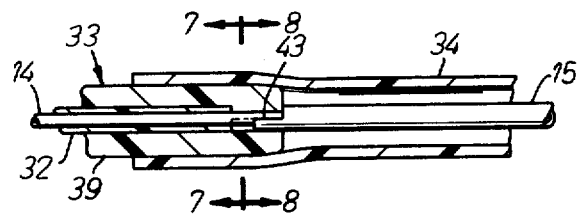
FIG. 6 is still another embodiment of the needle-inside, catheter placement assembly of the present invention when viewed as in FIG. 4.
Figure 7:
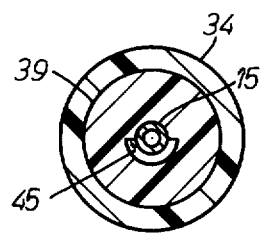
FIG. 7 is a cross-sectional view along the line 7—7 in FIG. 6 of the assembly thereof.
Figure 8:
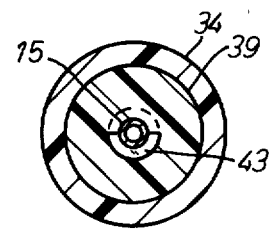
FIG. 8 is a cross-sectional view along the line 8—8 in FIG. 6 of the assembly thereof.
Figure 9:
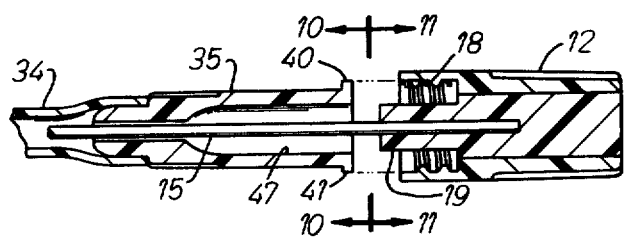
FIG. 9 is a cross-sectional view of the tube hub and needle hub of the assembly of FIG. 1.
Figure 10:
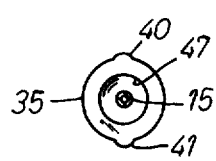
FIG. 10 is a cross-sectional view along the line 10—10 in FIG. 9 of the tube hub hereof.
Figure 11:
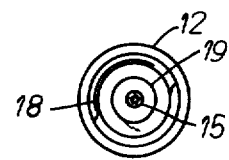
FIG. 11 is a cross-sectional view along the line 11—11 in FIG. 9 of the needle hub thereof.

FIGS. 6–8 depict still another embodiment of the complementary means associated with the lumen of tubular portion 39 and needle 11. In this embodiment, the shoulder 43 of needle 11 has both parallel and perpendicular surfaces to the axis thereof and is formed by removal of a semicircular segment from the distal end of second portion 15. As best seen in FIG. 7, the proximal end of the lumen of tubular portion 39 is enlarged to form a semicircular recess 45 complementary to shoulder 43 of needle 11. It will be readily apparent that numerous other embodiments for mechanically interlocking needle 11 and tubular portion 39 can be devised using various flanges, keys, pins, tongues, grooves, channels, slots, threads, etc.

On assembly, needle 11 is inserted into catheter unit 31 until the complementary means associated with the lumen of tubular portion 39 and shoulders of needle 11 meet and mechanically interlock. When that mechanical interlock has been achieved, the bevel at distal end 13 of needle 11 will be facing upwardly and projecting from the distal end of catheter 32 a chosen predetermined distance. The mechanical interlock will also prevent further distal movement of needle 11 with respect to catheter unit 31. Rotational misalignment or rotational movement of needle 11 with respect to catheter unit 31 is likewise prevented.

Proximal movement of needle 11 with respect to catheter unit 31 is prevented by the removable connection of tube hub 35 and needle hub 12. As best seen in FIGS. 12 and 14, flexible tubing 34 is stretched proximally, until projection 19 of needle hub 12 is inserted into the female adapter of tube hub 35 and hub ears 40, 41 juxtaposed with thread 18 of needle hub 12 after assembling of needle 11 and catheter unit 31. Because the complementary means associated with the lumen of tubular portion 39 and needle 11 will not allow relative rotation of needle 11 and catheter unit 31, threading ears 40, 41 onto complementary thread 18 causes flexible tubing 34 to twist and stretch until it is taut, thereby preventing proximal movement of needle 11 with respect to catheter unit 31 due to stretching of flexible tubing 34 during placement of the catheter into a patient.

Figure 16:
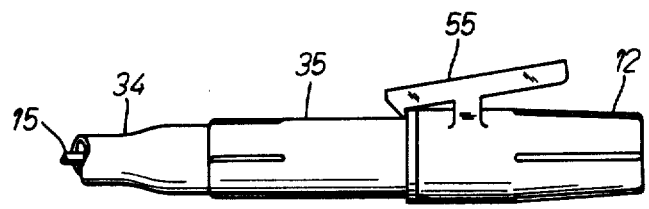
FIG. 16 is a front-elevational view of the tube hub and needle hub of another embodiment of the catheter placement assembly of this invention.
Figure 17:
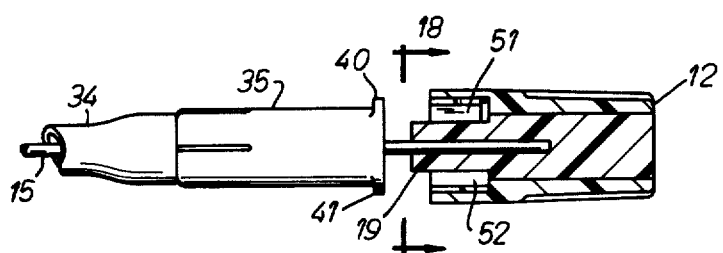
FIG. 17 is a front-elevational view of the tube hub and needle hub of still another embodiment of the catheter placement assembly of this invention, showing the needle hub in cross-section.
Figure 18:
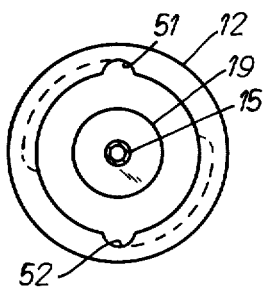
FIG. 18 is a cross-sectional view along the line 18—18 in FIG. 17 of the needle hub thereof.
Figure 19:
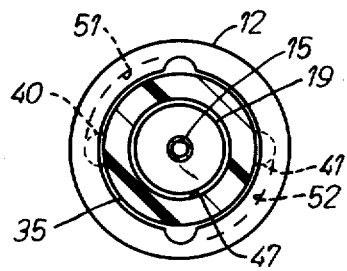
FIG. 19 is a view similar to FIG. 18 after the tube and needle hubs of the embodiment of FIG. 17 have been removeably connected together.

Alternative means of stretching flexible tubing 34 by removably connecting tube hub 35 and needle hub 12 will be readily apparent. One such alternate would be to provide L-shaped channels or slits 51, 52 in needle hub 12 complementary to ears 40, 41, as shown in FIG. 17. Another alternative would be to provide a pawl or lever 55 on needle hub 12 adapted to engage the collar of tube hub 35, as shown in FIG. 16.

In use, it is anticipated that the catheter placement assembly 9 will be inserted into a patient by pinching flexible wings 36, 37 together to provide a finger grip and inserting the distal end of needle 11 and catheter 32 into the patient's vein in accordance with conventional venipuncture techniques well known in the medical practice. After the vein has been entered, aperture 17 will allow blood to flow, or flashback, to flexible tubing 34 where it will readily be visible to indicate that the vein has been entered.

After the venipuncture has been achieved, the person inserting the assembly into the patient continues to grip wings 36, 37 in one hand and uses the other hand to disconnect needle hub 12 from tube hub 35. Needle 11 is then withdrawn from catheter unit 31 and discarded. Catheter 32 is fully inserted into the vein, wings 36, 37 are then taped to the patient, a safety loop formed with flexible tubing 34 and an intravenous solution set attached to tube hub 35 in accordance with conventional techniques of the medical practice.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

I claim:

1. In an intravenous catheter assembly including
   (1) a catheter unit comprising:
      (a) a flexible plastic catheter having a distally tapered distal end,
      (b) a winged catheter insertion means having a lumen therethrough, the proximal end of said catheter in communication with said lumen of said catheter insertion means via its distal end,
      (c) a flexible tubing having its distal end in communication with said lumen of said catheter insertion means via its proximal end,
      (d) a tube hub having a lumen therethrough, the proximal end of said flexible tubing in communication with said lumen of said tube hub via its distal end, and
   (2) a needle inserted through said catheter, winged catheter insertion means, flexible tubing and tube hub, said needle having a sharpened distal end extending beyond said distal end of said catheter and a proximal end attached to a needle hub; the improvement which comprises:
   complementary means associated with said lumen of said winged catheter insertion means and said needle mechanically interlocked to provide axial and rotational alignment of said needle relative to said catheter unit at all times.

2. The intravenous catheter assembly defined in claim 1, wherein said complementary means include a radially extending shoulder on said needle.

3. The intravenous catheter assembly defined in claim 2, wherein said needle comprises a first portion extending a predetermined distance from said distal end toward said proximal end and coaxially joined to a second portion having a greater outer diameter than the outer diameter of said first portion, whereby said shoulder on said needle is formed between said first and second portions.

4. The intravenous needle assembly defined in claim 3, wherein said first portion has a lumen therethrough in communication with a lumen in said second portion and said second portion has an aperture through its sidewall opening to said lumen thereof to allow blood to flashback through said needle into said flexible tubing.

5. The intravenous needle assembly defined in claim 3, wherein said radially extending shoulder on said needle has both parallel and perpendicular surfaces to the axis of said needle.

6. The inravenous needle assembly defined in claim 3, wherein said radially extending shoulder on said needle is oblique to the axis of said needle.

7. The intravenous needle assembly defined in claims 2, 5 or 6 wherein said proximal end of said winged catheter insertion means has an external surface surrounding said lumen and complementary to said shoulder on said needle.

8. The intravenous needle assembly defined in claims 2, 5 or 6 wherein said proximal end of said winged catheter insertion means has an internal recess adjacent said lumen and complementary to said shoulder on said needle.

9. The intravenous needle assembly defined in claim 8 wherein said recess is semicircular.

10. The intravenous needle assembly defined in claims 3 or 4, wherein the inner diameter of said flexible tubing is greater than the inner diameter of said catheter.

11. The intravenous needle assembly defined in claims 1, 2 or 3 wherein said tube hub and needle hub are removably connected by means causing said flexible tubing to be stretched taut while said tube hub and needle hub are connected.

12. The intravenous needle assembly defined in claim 11, wherein the proximal end of said tube hub comprises a female adapter having outwardly extending ears and the distal end of said needle hub has internal threads complementary to said ears, whereby said tube hub can be threadably connected to said needle hub.

13. The intravenous needle assembly defined in claim 11, wherein the proximal end of said tube hub comprises a female adapter having outwardly extending ears and the distal end of said needle hub has L-shaped channels complementary to said ears, whereby said tube hub can be engagedly connected to said needle hub.

14. The intravenous needle assembly defined in claim 11, wherein the proximal end of said tube hub comprises a female adapter having a collar and the distal end of said needle hub has an integral pawl adapted to engage said collar, whereby said tube hub can be engagedly connected to said needle hub.

* * * * *